United States Patent [19]

Gorka et al.

[11] Patent Number: 4,951,656
[45] Date of Patent: Aug. 28, 1990

[54] ORTHOPAEDIC STRUCTURES FROM POLYMERIC MATERIALS

[75] Inventors: Robert J. Gorka, Leominster; Ervin R. Dan, Lexington, both of Mass.

[73] Assignee: Polysar Financial Services S.A., Fribourg, Switzerland

[21] Appl. No.: 269,118

[22] Filed: Nov. 9, 1988

[51] Int. Cl.$^5$ ................................................ A61F 5/04
[52] U.S. Cl. ...................................... 128/90; 128/82.1; 128/89 R
[58] Field of Search ................ 525/314, 315, 243, 310; 128/82, 82.1, 89 R, 90, 89 A

[56] References Cited

U.S. PATENT DOCUMENTS

| | | | |
|---|---|---|---|
| 2,947,307 | 8/1960 | Hoppe | 128/90 |
| 3,326,211 | 6/1967 | Logue et al. | 128/82.1 X |
| 3,662,057 | 5/1972 | Webster et al. | 128/89 R X |
| 4,598,123 | 7/1986 | Cutter | 525/310 X |
| 4,666,809 | 5/1987 | Lindner et al. | 525/310 X |
| 4,821,708 | 4/1989 | Guignard et al. | 128/82.1 |

OTHER PUBLICATIONS

Warm in Form TM, Thermo Mod Medical Products, Inc., 1974.

Primary Examiner—Robert A. Hafer
Assistant Examiner—Kevin G. Rooney
Attorney, Agent, or Firm—Stevens, Davis, Miller & Mosher

[57] ABSTRACT

Orthopaedic structures, and processes for making the same, are provided in which the orthopaedic structure comprises a polymeric material which contains a block copolymer having grafted to it styrene, an alkyl acrylate and optionally methyl methacrylate. The orthopaedic structures are substantially transparent, formable and reformable at temperatures of about 45° to about 65° C. and are essentially rigid at ambient temperatures.

4 Claims, No Drawings

ORTHOPAEDIC STRUCTURES FROM POLYMERIC MATERIALS

BACKGROUND OF THE INVENTION

Orthopaedic structures of various types and made of various materials are well known. An orthopaedic structure is used to support and surround a body part which may be injured, diseased or which requires support and the term accordingly refers to casts, therapeutic splints, braces, jackets, shoe inserts, protective sport pads, stump sockets and the like.

Generally, orthopaedic structures have been made from cloth bandage material in combination with Plaster of Paris or from Plaster of Paris alone. The structure is generally prepared by rolling a water-wetted bandage impregnated with Plaster of Paris about the body portion to be encased and allowing it to dry to rigidity (which usually takes up to one day). Making such structures is clearly messy, time-consuming and awkward and Plaster of Paris structures are well known to be heavy. Also, Plaster of Paris structures cannot be altered once made.

A more recent form of orthopaedic structure uses polymers such as a crystalline high molecular weight conjugated diolefin polymer (e.g. trans-1, 4 polyisoprene) or a polycaprolactone mixed with a filler such as titanium dioxide and/or silica. Such structures do not have the required strength characteristics for all orthopaedic uses. In addition they lack clarity.

DESCRIPTION OF THE PRIOR ART

U.S. Pat. No. 3,656,476 describes orthopaedic structures which are made from crystalline high molecular weight conjugated diolefin polymers mixed with a filler. The polymer is preferably trans-1, 4-polyisoprene. U.S. Pat. No. 4,680,337 discloses thermoplastic polymers suitable for containers and packaging, which comprise styrene, an acrylate, a methacrylate and a block copolymer. Such polymers are essentially transparent. U.S. Pat. Nos. 3,400,175, 3,922,321, 4,100,227, 4,100,228 and 4,115,478 teach methods of making various impact resinous polymers from one or more vinyl aromatic monomers, acrylate-type monomers and rubbery polymers, some of which are transparent. Chem. Abs. 82 58952 w, 95 116246 a and 58 10365 f are abstracts of further methods to prepare similar types of polymers. U.S. Pat. No. 4,080,406 describes transparent, impact resistant polymers made by polymerizing a vinyl aromatic monomer, a methacrylate and a $C_4$–$C_{12}$ alkyl methacrylate in the presence of a butadiene-styrene block copolymer for use in packaging and as containers.

The polymers described in the prior art do not have the balance of properties required for use in an orthopaedic structure.

SUMMARY OF THE INVENTION

Orthopaedic structures and methods of producing the same are provided in which the orthopaedic structures are substantially transparent, formable and reformable at temperatures of from about 45° to about 65° C., essentially rigid at ambient temperatures of below about 30° C. and which have a desirable balance of strength properties, which comprise a polymeric material comprising as the essential components, all parts being parts by weight, (A) from about 55 to about 70 parts of styrene, (B) from 0 to about 10 parts of methyl methacrylate, (C) from about 15 to about 40 parts of a $C_2$–$C_8$ alkyl acrylate and (D) from about 2 to about 15 parts of one or more block copolymer selected from the group consisting of styrene-butadiene, styrene-butadiene-styrene and styrene-isoprene block copolymers having a weight average molecular weight of not less than about 75,000 and a styrene content of about 20 to about 50 weight per cent, for a total of 100 parts, said polymeric material being produced by the polymerization of A, B and C in the presence of D to produce a polymeric material containing said block copolymer having grafted thereto at least a portion of A, B and C.

Further, there is provided a method of producing an orthopaedic structure which is substantially transparent, formable and reformable at temperatures of from about 40° to about 65° C., essentially rigid at ambient temperatures of below about 30° C. and which has a desirable balance of strength properties, which method comprises:
  (a) providing a sheet of polymeric material,
  (b) heating said sheet to a temperature of from about 45° to about 65° C.,
  (c) shaping said heated sheet to form the orthopaedic structure about the desired part of the body, and
  (d) allowing the so-shaped orthopaedic structure to cool to below about 30° C.,
wherein said polymeric material comprises as the essential components, all parts being parts by weight, (A) from about 55 to about 70 parts of styrene, (B) from 0 to about 10 parts of methyl methacrylate, (C) from about 15 to about 40 parts of a $C_2$–$C_8$ alkyl acrylate and (D) from about 2 to about 15 parts of one or more block copolymer selected from the group consisting of styrene-butadiene, styrene-butadiene-styrene and styrene-isoprene block copolymers having a weight average molecular weight of not less than about 75,000 and a styrene content of about 20 to about 50 weight per cent, for a total of 100 parts, said polymeric material being produced by the polymerization of A, B and C in the presence of D to produce a polymeric material containing said block copolymer having grafted thereto at least a portion of A, B and C.

Still further there is provided a method of producing an orthopaedic structure which is substantially transparent, formable and reformable at temperatures of from about 45° to about 65° C., essentially rigid at ambient temperatures of below about 30° C. and which has a desirable balance of strength properties, which method comprises:
  (a) providing a polymeric material in the shape of an orthopaedic pre-form of standard shape and size,
  (b) heating said pre-form to a temperature of from about 45° to about 65° C.,
  (c) fitting said heated pre-form about the desired part of the body,
  (d) adjusting said heated pre-form to the desired shape about the desired part of the body,
  (e) optionally removing surplus polymeric material from said shaped pre-form, and
  (f) allowing the shaped pre-form to cool to below about 30° C.,
wherein said polymeric material comprises as the essential components, all parts being parts by weight, (A) from about 55 to about 70 parts of styrene, (B) from 0 to about 10 parts of methyl methacrylate, (C) from about 15 to about 40 parts of a $C_2$–$C_8$ alkyl acrylate and (D) from about 2 to about 15 parts of one or more block copolymer selected from the group consisting of styrene-butadiene, styrene-butadiene-styrene and styrene-isoprene block copolymers having a weight average molecular weight of not less than about 75,000 and a styrene content of about 20 to about 50 weight per cent, for a total of 100 parts, said polymeric material being produced by the polymerization of A, B and C in the presence of D to produce a polymeric material containing said block copolymer having grafted thereto at least a portion of A, B and C.

DETAILED DESCRIPTION OF THE INVENTION

The novel orthopaedic structures of the present invention comprise the polymeric materials as defined. In order to meet the needs of the marketplace, a number of properties for such orthopaedic structures are desirable. Preferred requirements for orthopaedic structures include that the structure be substantially transparent, especially while in the stage of being formed, in order that the body member or any wound or surgical incision can be observed. Also included is the requirement that the structure be readily formable and preferably also be readily reformable. The body can withstand temperatures up to about 60° to 65° C. without serious discomfort—formability and reformability at temperatures from about 45° to about 65° C., preferably from about 55° to about 65° c, is therefore desirable. If the temperature of formability is below about 45° C., the structure may be locally exposed to such a temperature and become deformed. Reformability allows the medical practitioner to adjust the structure as necessary without removing the orthopaedic structure and replacing it. The orthopaedic structure should be essentially rigid at ambient temperatures of below about 30° C. so that the required support is provided over temperature ranges normally encountered in every day life. The orthopaedic structure must have a desirable balance of strength properties—that is, it must possess a high enough tensile strength, flexural strength and flexural modulus to provide the required support. It is desirable that the material of the orthopaedic structure flow reasonably and be soft enough to allow formability and reformability, but yet not flow such as to be uncontrollable, at about 45° to about 65° C.

The selection of a polymeric material to meet this balance of properties is difficult. The most extensively used polymeric materials have been trans-1,4-polyisoprene and polycaprolactone—these polymers are mixed with filler, usually silica and titanium dioxide, and are thereby not transparent. Many polymeric materials have softening temperatures which are far too high to be used with the body. Many polymeric materials have high strength properties but cannot meet the other requirements especially the formability temperature.

In the course of the experimental work which finally lead to the present invention, other polymeric materials were evaluated but were found not to have the overall required balance of properties. Thus, polymers of methyl methacrylate containing a small amount of rubber (methyl methacrylate content about 90 to 95 weight per cent and rubbery polybutadiene or styrene-butadiene polymer content about 5 to 10 weight per cent) when mixed with about 20 to 30 parts by weight, per 100 parts by weight of methyl methacrylate polymer, of a suitable plasticizer were found to have the required strength, transparency and rigidity properties but did not have the required formability and reformability characteristics and the plasticizer tended to exude out of the material. Polymers made by polymerizing from about 30 to about 45 parts by weight of styrene, from about 15 to about 40 parts by weight of methyl methacrylate and from 5 to about 25 parts by weight of butyl acrylate in the presence of about 2 to 15 parts by weight of a block copolymer required the presence of at least 2 and up to about 25 parts by weight, per 100 parts by weight of polymer, of a plasticizer to be partially formable or reformable at the desired temperatures and the plasticizer tended to exude out of the material.

The polymeric material used in the orthopaedic structure of the present invention preferably comprises, all parts being parts by weight, from about 55 to about 70, most preferably from about 58 to about 65, parts of styrene, from 0 to about 5 parts, and most preferably from about 2 to about 3 parts, of methyl methacrylate, from about 20 to about 40 parts, and most preferably from about 25 to about 35 parts, of an alkyl acrylate selected from ethyl acrylate, butyl acrylate and ethylhexyl acrylate, most preferably butyl acrylate, and from about 3 to about 12 parts, most preferably from about 5 to about 10 parts, of block copolymer, the block copolymer suitably being selected from a butadiene-styrene tapered block copolymer having a styrene content of about 40 weight per cent and a weight average molecular weight of about 85,000 and commercially available as Stereon 840 and a butadiene-styrene radial block copolymer having a styrene content of about 30 weight per cent and a weight average of about 200,000 and commercially available as Finaprene 411, or mixtures thereof. Such polymeric materials may also contain minor amounts of up to 3 or even up to 5 parts by weight, per 100 parts by weight of polymer, of a plasticizer such as the alkyl benzyl phthalates, especially butyl benzyl phthalate.

Such a polymeric material may be made by polymerization wholly in bulk or in a bulk-suspension system. In a bulk polymerization system, the block copolymer dissolved in styrene and the methyl methacrylate (if present) and acrylate monomer are fed into an agitated reaction vessel maintained at a temperature of about 80° to about 100° C. When temperature equilibrium is established, a small amount of one or more free radical source, such as an organic peroxide, organic hydroperoxide or organic perester, is added to initiate polymerization. Suitable free radical sources include benzoyl peroxide, dicumyl peroxide, lauroyl peroxide, t-butyl hydroperoxide and t-butyl perbenzoate. Polymerization is continued for between 3 and 6 hours and the polymerizing mixture is then transferred to the first of two or three reactors connected in series and maintained at temperatures from about 105° to about 160°. Such reactors are preferably equipped with agitation means, the first such reactor will generally be maintained at about 105° to about 120° C., the second (of a series of two reactors only) will be maintained at about 125° to about 160° C. and the second (of a series of three reactors) will be maintained at about 115° to about 125° C. and the third reactor will be maintained at about 125° to about 150° C. The polymerizing mixture will be maintained in this series of reactors for a time of about 2 to about 6 hours and the conversion of the polymerizable monomers is generally from about 60 to about 90%. The product from the last of the series of reactors is passed through a preheating means, to heat it to about 200° to about 240°, to a devolatization chamber operated at about 220° to about 260° C. and a pressure of about 10 to about 40mm of mercury whereby residual monomers are essentially removed from the polymer. The so-formed polymer may then be pelletized, cooled and packaged.

In a bulk-suspension polymerization process, the block copolymer dissolved in styrene and the methyl methacrylate (if present) and acrylate monomer are fed into an agitated reaction vessel maintained at a temperature of about 80° to about 99° C. When temperature equilibrium is established, a small amount of one or more free radical source, such as an organic peroxide, organic hydroperoxide or organic perester, is added to initiate polymerization. Suitable free radical sources include benzoyl peroxide, dicumyl peroxide, lauroyl peroxide, t-butyl hydroperoxide and t-butyl perbenzoate. Incremental proportions of the monomers may be added during this stage of the polymerization. Polymerization is continued until the polymerizing mixture contains about 35 to about 40 per cent by weight of polymer.

The product from the reactor is cooled, suspended in water in the presence of one or more suspending agents such as partially hydrolyzed polyvinyl acetate and additional free radical source is added. The suspension is then passed to an agitated reactor also equipped with temperature control means and the contents of the reactor are polymerized usually in two to four stages. The first stage will be at a temperature of about 90° to about 100° C. for a time of about 1 to about 3 hours, a second stage will be at a temperature of about 105° to about 115° C. for about 1 to about 3 hours and a third or fourth stage will be at a temperature of about 115° to about 130° C. for about 1 to about 3 hours. The polymer is then separated from the aqueous phase, washed and dried to remove any remaining monomers and water.

The polymeric materials are used to make the orthopaedic structures. Suitably, the polymeric materials are provided as sheets or as pre-forms. The polymeric material is a thermoplastic material and can be readily formed into sheets by molding, extrusion or the like. Suitable sheets would generally have a thickness of from about one-eighth inch (about 0.3 cm) up to about one-quarter inch (about 0.6 cm) and may be of convenient size (i.e. length and width) for shipment or for use. The size of the sheet is not critical. Such sheets may also be produced having small holes throughout, which holes allow breathing and vapor transmission to occur when used as the orthopaedic structure. Pre-forms may readily be prepared from sheets or from the polymeric material in pellet or small particle form. A pre-form may be for use as an orthopaedic structure for an arm, or for a leg, or for some other body part for a small, medium or large body or for a child or a teenage person or an adult. Thus, the appropriate pre-form may be made to minimize the initial work of transforming a sheet to the general shape of the orthopaedic structure desired. Such pre-forms may readily be made such as by molding.

If a polymeric material in sheet form is used, it is warmed to a workable condition, such as by immersion in hot water, heating in an oven or blowing with hot air. Workable conditions are generally from about 45° to about 65° C. temperature range. The warm sheet is then shaped about the body part to be encompassed and allowed to cool to below about 30° C. Any changes in shape, major or minor, may readily be made by heating the area to be changed, such as with hot air, re-molding and cooling. Thus, the orthopaedic structure is readily formed. If a pre-form is used, once the suitable shape and size has been selected, the pre-form is warmed to about 45° to about 65° C., the warmed pre-form is then adjusted to closely fit the body part to be encompassed and then allowed to cool to below about 30° C. In one embodiment, the pre-form is shaped to totally enclose the desired part of the body. In another embodiment, the pre-form is shaped to partially enclose the desired body part and is held in place by a suitable strap or bandage. It is possible that there may be more polymeric material than is needed for the orthopaedic structure—then, optionally, surplus polymeric material may readily be removed, such as by cutting or by filing. Further modification of the fit of the orthopaedic structure may readily be achieved by local heating, as with hot air, to about 45° to about 65° C., re-molding and cooling.

The orthopaedic structures are substantially transparent, and accordingly, it is possible to observe the body encompassed by the orthopaedic structure. The benefits of this are readily understood.

The orthopaedic structures have to have certain property characteristics. They have to be essentially rigid at ambient temperatures of below about 30° C.—the purpose of an orthopaedic structure is to maintain the body member in a fixed position and thereby rigidity of the orthopaedic structure is a requirement. They have to possess sufficient strength properties to maintain the body member in its fixed position and have to have sufficient impact strength so as not to be readily broken. Generally, it is desirable for the polymeric material of the orthopaedic structure to have a tensile strength of not less than about 3,000 psi and more preferably of not less than about 4,000 psi. It is desirable that the polymeric material not exhibit a yield under stress of less than the tensile strength. It is also desirable that the polymeric material have a tensile modulus of not less than about 200,000 psi and most preferably of not less than about 250,000 psi.

The following examples serve to illustrate the invention whereas the claims appended hereto define the scope of the invention.

EXAMPLE 1

This example serves to illustrate how to make polymeric material for use in the orthopaedic structure. A styrene-butadiene block copolymer Stereon 840 was dissolved in styrene to produce a solution containing 7 parts by weight of Stereon 840 per 40 parts by weight of styrene. To a 20 gallon reactor equipped with an agitator and a temperature control means was charged 45 pounds of the styrene-Stereon 840 solution, 21 pounds of butyl acrylate, 32 grams of dodecyl mercaptan and 55 grams of 70% benzoyl peroxide. The temperature of the contents of the reactor was raised to 85° C. thereby initiating polymerization. Increments of styrene and benzoyl peroxide were added as the polymerization was proceeding until a further 4 pounds of styrene and 20 grams of benzoyl peroxide had been added. The temperature was maintained at 85° for 2 hours, then at 90° C. for 2 hours and then at 95° C for 2 hours at which time the solids content was about 38 weight per cent. After cooling, 31 pounds of distilled water was added, 28 grams of each of benzoyl peroxide and tert-butyl perbenzoate were added and 300 ml were added of a 7 per cent solution of polyvinyl alcohol in water as suspending agent. The reactor was heated up to 90° C. to initiate further polymerizations and maintained at 90° C. for 1.5 hours, then raised to 110° C. for 2 hours and finally raised to 120° C. for 3 hours. After cooling, the particles of polymer were washed and then dried in a warm air oven maintained at about 45° C. The polymer was fed to an extruder operated at 175° C. and sheets of polymeric material were produced which contained, based on 100 parts by weight of the polymer, about 63 parts by weight of styrene, about 30 parts by weight of butyl acrylate and about 7 parts by weight of block copolymer hereinafter PM #1). Similarly, sheets were produced from polymeric material containing about 4 weight per cent of benzyl butyl phthalate (PM #1A).

EXAMPLE 2

Following the same procedure as described in Example 1, polymeric materials, in sheet form, were prepared and contained, per 100 parts by weight of polymer, about 60 parts by weight of styrene, about 30 parts by weight of butyl acrylate, about 3 parts by weight of methyl methacrylate and about 7 parts by weight of block copolymer Stereon 840 (PM #2). Sheets were also prepared from the polymeric material containing about 2 weight per cent of benzyl butyl phthalate (PM #2A).

EXAMPLE 3

Using essentially the same procedures as described in Example 1, a further two polymeric materials were prepared. One (PM #3) contained about 65 parts by weight of styrene, about 30 parts by weight of butyl acrylate and about 5 parts by weight of block copolymer Stereon 840. A portion of this polymeric material (PM #3A) was mixed with 5 weight per cent of benzyl butyl phthalate. The second (PM #4) contained about 70 parts by weight of styrene, about 25 parts by weight of butyl acrylate and about 5 parts by weight of block copolymer Stereon 840.

EXAMPLE 4

Following essentially the procedure of Example 1, a polymeric material was prepared which contained 59 weight percent of styrene, 32 weight per cent of butyl acrylate and 9 weight per cent of a mixture of essentially equal parts by weight of Stereon 840 and Finaprene 411. Such polymeric material was formed into sheets for further use (PM #5).

EXAMPLE 5

Using the polymeric material of Example 4 (PM #5), sheets were prepared, in a commercial sheet extruder at a barrel temperature of about 175° C., with a width of about 48 inches, some having a thickness of about 0.25 inch and some having a thickness of about 0.125 inch. The 0.25 inch thick sheet was preheated in an oven at a temperature of about 175° C. and then vacuum thermoformed over a mold to form a chech socket for use at the stump end of an amputated leg.

EXAMPLE 6

The 0.125 inch thick sheet of Example 5 was thermoformed at 60° to 70° C. into various corrective heel and sole support shoe inserts. Such shoe inserts were found to have long lives and not to distort during use.

EXAMPLE 7

The 0.125 inch thick sheet of Example 5 was cut to suitable size and then immersed in water at about 65 C. when softened, the sheets were used as casts by placing about arms or hands, shaping to conform with the arm or hand to be fitted and then allowed to cool to about 25° C. Surplus sheet material was cut off while the polymeric material was still soft. It was found that the sheet material had an adequate working time to allow the cast to be properly fitted. One such cast was subsequently re-softened by heating with a hot hair drier and re-shaped to more accurately conform to the body part and then allowed to cool to about 25° C. On cooling the casts were essentially rigid, substantially transparent and had more than sufficient strength to retain the body part in a fixed position.

EXAMPLE 8

Similar to Example 7, sheets of polymeric materials PM #1, PM #1A, PM #2, PM #2A, PM #3, PM #3A, and PM #4 were formed into casts about portions of an arm or a leg and the casts were found to be fully satisfactory. The sheets of polymeric materials PM #1A. PM #2A, and PM #3A were found to be somewhat more readily moldable, presumably because of the presence in them of the small amount of plasticizer.

EXAMPLE 9

Portions of polymeric material PM #1, in pellet form, were used to thermo form a pre-form for use over the lower arm, the wrist and hand. The pre-form had the approximate shape of one half of the lower arm, wrist and the back of the hand and had extensive excess sheated material. The pre-form was warmed in a hot air oven to a temperature of about 60° to about 65° C., placed about the lower arm, wrist and hand and shaped around the body parts. In one instance, the shaping was such as to form a complete cast about the lower arm, wrist and hand. In a second case, the shaping was such as to cover one half to two thirds of the circumference of the lower arm, wrist and hand and was held onto the body parts by wrapping with a retaining bandage—this allowed the cast to be removed periodically.

What is claimed is:

1. A method of producing an orthopaedic structure which is substantially transparent, formable and reformable at temperatures of from about 45° to about 65° C., essentially rigid at ambient temperatures of below about 30° C. and which has a desirable balance of strength properties, which method comprises:
    (a) providing a sheet of polymeric material,
    (b) heating said sheet to a temperature of from about 45° to about 65° C.,
    (c) shaping said heated sheet to form the orthopaedic structure about the desired part of the body, and
    (d) allowing the so-shaped orthopaedic structure to cool to below about 30° C.,
wherein said polymeric material comprises as the essential components, all parts being parts by weight, (A) from about 55 to 70 parts of styrene, (B) from 0 to about 10 parts of methyl methacrylate, (C) from about 15 to about 40 parts of a $C_2$–$C_8$ alkyl acrylate and (D) from about 2 to about 15 parts of one or more block copolymer selected from the group consisting of styrene-butadiene, styrene-butadiene-styrene and styrene-isoprene block copolymers having a weight average molecular weight of not less than about 75,000 and a styrene content of about 20 to about 50 weight per cent, for a total of 100 parts, said polymeric material being produced by the polymerization of A, B and C in the presence of D to produce a polymeric material containing said block copolymer having grafted thereto at least a portion of A,B, and C.

2. A method of producing an orthopaedic structure which is substantially transparent, formable and reformable at temperatures of from about 45° to about 65° C., essentially rigid at ambient temperatures of below about 30° C. and which has a desirable balance of strength properties, which method comprises:
(a) providing a polymeric material in the shape of an orthopaedic pre-form of standard shape and size,
(b) heating said pre-form to a temperature of from about 45° to about 65° C.,
(c) fitting said heated pre-form about the desired part of the body,
(d) adjusting said heated pre-form to the desired shape about the desired part of the body,
(e) optionally removing surplus polymeric material from said shaped pre-form, and
(f) allowing the shaped pre-form to cool to below about 30° C.,
wherein said polymeric material comprises as the essential components, all parts being parts by weight, (A) from about 55 to about 70 parts of styrene, (B) from 0 to about 10 parts of methyl methacrylate, (C) from about 15 to about 40 parts of $C_2$–$C_8$ alkyl acrylate and (D) from about 2 to about 15 parts of one or more block copolymer selected from the group consisting of styrene-butadiene, styrene-butadiene-styrene and styrene-isoprene block copolymers having a weight average molecular weight of not less than about 75,000 and a styrene content of about 20 to about 50 weight per cent, for a total of 100 parts, said polymeric material being produced by the polymerization of A, B and C in the presence of D to produce a polymeric material containing said block copolymer having grafted thereto at least a portion of A, B, and C.

3. The method of claim 2 wherein the pre-form is shaped to totally enclose the desired part of the body.

4. The method of claim 2 wherein the pre-form is shaped to partially enclose the desired part of the body and is held in place by a suitable strap or bandage.

* * * * *